(12) United States Patent
Mazen et al.

(10) Patent No.: US 9,201,023 B2
(45) Date of Patent: Dec. 1, 2015

(54) SYSTEM FOR MEASURING A SPACING ZONE IN A SUBSTRATE

(71) Applicant: COMMISSARIAT A L'ENERGIE ATOMIQUE ET AUX ENERGIES ALTERNATIVES, Paris (FR)

(72) Inventors: Frédéric Mazen, Grenoble (FR);
François Rieutord, Saint Egreve (FR);
Jean-Daniel Penot, Grenoble (FR);
Philippe Montmayeul, Bernin (FR)

(73) Assignee: COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 0 days.

(21) Appl. No.: 14/386,869

(22) PCT Filed: Mar. 12, 2013

(86) PCT No.: PCT/FR2013/050517
§ 371 (c)(1),
(2) Date: Sep. 22, 2014

(87) PCT Pub. No.: WO2013/140065
PCT Pub. Date: Sep. 26, 2013

(65) Prior Publication Data
US 2015/0055122 A1 Feb. 26, 2015

(30) Foreign Application Priority Data

Mar. 21, 2012 (FR) ...................................... 12 52507

(51) Int. Cl.
*G01N 21/00* (2006.01)
*G01N 21/95* (2006.01)
*H01L 21/66* (2006.01)
*G01B 11/14* (2006.01)
*G01P 3/36* (2006.01)
*H01L 21/762* (2006.01)

(52) U.S. Cl.
CPC ............ *G01N 21/9505* (2013.01); *G01B 11/14* (2013.01); *G01P 3/36* (2013.01); *H01L 21/76254* (2013.01); *H01L 22/12* (2013.01); *G01N 21/9501* (2013.01)

(58) Field of Classification Search
CPC ...... G01N 21/9505; G01B 11/14; G01P 3/36; H01L 21/76254; H01L 22/12
USPC ..................... 356/496, 503, 505, 237.1, 237.2
See application file for complete search history.

(56) References Cited

U.S. PATENT DOCUMENTS

| | | | |
|---|---|---|---|
| 5,517,861 A * | 5/1996 | Haas ...................... | G01N 3/068 356/237.1 |
| 8,559,018 B2 * | 10/2013 | Takeda ................... | G01B 11/18 356/237.1 |

*Primary Examiner* — Gregory J Toatley
*Assistant Examiner* — Hina F Ayub
(74) *Attorney, Agent, or Firm* — Oliff PLC

(57) ABSTRACT

This system for measuring the propagation of a zone of separation between a first portion and a second portion of at least one substrate includes: a module for emitting at least two incident beams each of which illuminates a separate point on the substrate, the at least two incident beams being able to pass through the first portion and the zone of separation and meet the second portion in such a way that each of them generates at least one first emergent beam Fe originating from the interface between the first portion and the zone of separation, and at least one second emergent beam originating from the interface between the zone of separation and the second portion; a detecting module for detecting light intensity values resulting from interference between the first and second emergent beams; and a computer for determining the conditions of the propagation of the zone of separation.

16 Claims, 1 Drawing Sheet

SYSTEM FOR MEASURING A SPACING ZONE IN A SUBSTRATE

The present invention relates to a system for measuring the propagation of a spacing zone between a first portion and a second portion of at least one substrate. Moreover, the present invention relates to a device suitable for the propagation of this spacing zone. Finally, the present invention relates to a method for measuring the propagation of this spacing zone.

Certain industrial processes are based on the fracture of a substrate of brittle material such as:

the Smart Cut™ process, which allows to detach a thin film of a substrate by rupture of the material, the rupture being induced by the implantation of gaseous ionic species in the substrate, the cleaving process for separating different parts on a material wafer also called 'wafer' in the Anglo-Saxon terminology.

The control of the fracture speed and more generally of the cracking dynamics is necessary because often the facies of rupture, that is to say the roughness of the surfaces of the fractured material, is conditioned by the dynamic aspects of the propagation of the fracture front.

Furthermore, it may be useful to control the way in which a rupture propagates through a material in order for example to be able to predict or impose a rupture path.

The observation of the fracture can be obtained by rupture gauges. These gauges consist of a small network of wires located in the provided path of the crack that break at the same time as the material during the passage of the fracture front. But this network is bonded to a lateral side of the substrate to be fractured so much so that the speed of the opening is only measured on this same side of the substrate. This technique therefore only provides information on a local speed. Moreover, the bonding of the network to the substrate can lead to the disturbance of the propagation of the fracture wave.

The high speed photography method also allows observing the progression of the crack front from a lateral face of the substrate. This method is effective during the fracture of relatively soft and transparent materials. Elasto-optical effects can also be combined with high speed photography in order to obtain information on the stress field in the vicinity of the crack front. However, when the crack of a centimeteric substrate moves at a speed of a few km/s, for example from 1 to 4 km/s for a fracture in the silicon, it is necessary to use frequencies in the range of one million images per second. This frequency is extremely difficult to achieve and is very expensive. Furthermore, only materials transparent to visible light can be used for a characterization of the entire plane of the fracture.

There are also observation methods of facet of the facies of rupture of the surface of the fractured substrates but these methods limit the possibility of studying the path and speed of the crack after passage of the fracture.

Similarly, for certain industrial processes, it can also be interesting to study the way in which two surfaces of material come closer to each other. The observation of a relatively slow bonding wave, the speed of which is for example comprised between a few mm/s and a few cm/s, is usually made using cameras. But for some bondings, in particular vacuum direct bonding, the bonding wave propagates very quickly, for example at a speed in the range of a few km/s. However, the currently available and still inexpensive methods do not allow characterizing a bonding wave in this range of speed.

One of the aims of the invention is to overcome one or more of these drawbacks. To this end, and according to a first aspect, the invention relates to a measuring system for measuring the propagation of a spacing zone C between a first portion and a second portion of at least one substrate, the measuring system comprising:

an emitting module for emitting at least two spatially distinct incident beams Fi each illuminating a region of the substrate, said emitting module being arranged so that the at least two incident beams Fi can pass through the first portion, the spacing zone C and meet the second portion, so that each generates at least a first emergent beam Fe originating from the interface between the first portion and the spacing zone C, and at least a second emergent beam Fe originating from the interface between the spacing zone C and the second portion, a detecting module for detecting luminous intensity, arranged so as to detect the values of the resulting luminous intensity at a given point of the interference between the first and second emergent beams Fe, a calculator arranged to determine at least one parameter representative of the conditions of the propagation of the spacing zone C from the time variations of the luminous intensity detected by the detecting module.

In the present application, by the expression 'a spacing zone C between a first portion and a second portion', it is meant the zone extending between these two portions and which may take the shape of a dihedral formed from the point of contact between the surfaces of the first portion and the second portion.

In the present application and within the scope of the bonding between a first and a second portion, it is meant by the expression 'propagation of a spacing zone', the displacement of the spacing zone C ahead of the propagation of the bonding due to the approximation of the surfaces of the two portions.

In the present application and within the scope of the fracture, by the expression 'propagation of a spacing zone' it is meant the progression of the spacing zone C behind the passage of the fracture front due to the distance of the surfaces between the two portions of the substrate.

By the expression 'a beam that can meet the second portion' it is meant a 'beam which can illuminate the second portion' the beam whether reflected or partially transmitted through the second portion.

This device is simple to set up, inexpensive and allows measuring very high speeds of propagation of a spacing zone C, which is especially useful when observing portions made of brittle materials and of high stiffness such as silicon and ceramics for example. Moreover, this device is highly sensitive since it allows measuring very low thicknesses of spacing zone C between the two portions, in the range of for example a few wavelength fractions. The measuring system therefore can detect the exact instant at which the fracture or the bonding takes place. Furthermore, this device is very accurate because it allows determining the spacing or approximation profile between the two portions by means of interferometric measurements. It also allows performing a contactless measurement, without altering the substrate(s) to be studied.

By the expression 'at least two spatially distinct beams' it is meant beams the paths of which do not coincide so that they illuminate each a localized region of the surface of the substrate. The illuminated regions are distinct and can therefore be situated at different locations on the entire surface of the substrate.

Preferably, the detecting module and the calculator are configured to determine the speeds of propagation of the spacing zone C between the first and second portions. The measuring system is therefore capable of measuring very high speeds of propagation of the spacing zone C ahead of the propagation of the bonding between the first and second portions of the substrate or behind the fracture front between the first and second portions of the substrate (in the range of a few km/s for example).

According to a particular embodiment, the at least two incident beams illuminate each a region of the substrate while being situated in different planes. This arrangement of non-coplanar beams allows detecting the occurrence and measuring the speed of propagation of the spacing zone C between different points distributed over the entire surface of the substrate.

Advantageously, the at least two incident beams are arranged so as to be coplanar so as to allow measuring the propagation of the spacing zone C in the direction of the plane of the beams.

This arrangement is favourable to the determination of the spacing profile between the first and second portions during the fracture between the first and second portions or the approximation profile during the bonding of the first and second portions. It is then possible to determine the intensity and the variation of the stresses submitted on the portions of the substrate during the fracture or the bonding and also to study and determine the mechanisms coming into play.

According to a particular embodiment of the invention, the emitting module comprises at least two light sources suitable for emitting beams. It is therefore possible to easily change the distance between the incident beams or their orientation by simple displacement of the light sources. This also allows facilitating the addition or the removal of a light source depending on the size of the substrate to be observed.

Preferably, the emitting module comprises a light source and at least one coupler, the light source and said at least one coupler being arranged such that said at least one coupler can separate the light emitted from the light source into at least two beams.

Advantageously, the emitting module comprises at least two and single-mode optical fibers and at least two collimators, the optical fibers being suitable for guiding the beams produced by said at least one coupler respectively up to the collimators, the collimators being suitable for producing the at least two incident beams. Therefore, the incident beams are guided without signal spreading up to the collimators that allow emitting a beam of parallel light rays. This arrangement allows moving the light source away from the measuring zone.

According to a possible embodiment, the light source is monochromatic, and comprises in particular a laser, such as an infrared laser diode suitable for the case of a silicon substrate.

Advantageously, the emitting module is arranged to generate at least two incident beams Fi that are monochromatic, coherent and intense so that the detected luminous intensity is greater than the noise of the detecting measurement. Typically, the luminous power of the beam is greater than 0.1 mW and is advantageously greater than 0.5, or even 1 mW.

Preferably, at least one incident beam is selected such that at least 10% of its luminous intensity can be emitted through the first portion so as to keep a sufficient luminous intensity to finely observe the variation of reflection and/or transmission when the beam passes through the spacing zone C.

According to a particular embodiment, the emitting module and the detecting module are arranged on the same side of said at least one substrate so as to detect the emergent beams when the measuring system operates in reflection, in particular when the incident beams are reflected by the second portion.

Advantageously, said at least one incident beam is also selected such that at least 10% of its luminous intensity may be transmitted through the encountered second portion by said at least one incident beam so that the emitting module and the detecting module are arranged on either side of said at least one substrate. It is therefore possible to detect the emergent beams when the device operates in emission. Moreover, thanks to this configuration, a plurality of substrates can be placed in a parallel manner and such that their main surfaces are perpendicular to the direction of the incident beams. The beams can then pass through all of the substrates. It is therefore possible to measure the propagation of the spacing zones in the substrate in a single measuring step.

Typically, the wavelength of said at least one incident beam is selected such that at least 10% of its luminous intensity can be transmitted through the second portion and/or the first portion.

Preferably, the detecting module comprises at least one luminous intensity receiver and at least one photodetector so as to convert the received values of the resulting luminous intensity at a given point of the interference between the first and second beams into an electrical signal.

According to one possibility, the measuring system comprises acquisition and recording devices of the electrical signal, such as a sampling device, for example a digital oscilloscope or an analog-digital converter card, so that it can store information serving in particular as a base to the calculation of the speed of propagation of the spacing zone C by the calculator.

Typically, the calculator comprises a processor.

According to one possibility, the acquisition and recording devices of the electrical signal are integrated into the calculator.

According to a second aspect, the invention relates to a device suitable for the propagation of a spacing zone C between a first portion and a second portion of at least one substrate, the device comprising a measuring bench, such as a furnace, a traction machine or a mechanical testing machine, equipped with means suitable for the induction of a fracture or a bonding between the first portion and the second portion and a measuring system for measuring the propagation of a spacing zone C, as previously described. This device allows to measure, in situ, parameters representative of the conditions of propagation of the spacing zone C on the measuring bench allowing the fracture or the bonding between the two portions. These parameters are for example the detection of the occurrence of fracture or the bonding, the speed of the fracture front or bonding front and the spacing or approximation profile between the two portions. This spacing profile takes an increasingly significant value in the case of the fracture and an increasingly small value, until it becomes zero during bonding. Once processed, these information allows determining the phenomena intervening during fracture or bonding, such as stresses submitted in the material and the mechanism of fracture or bonding.

According to one possibility, the measuring bench is a closed enclosure, in particular a tight furnace in order to be able to induce a vacuum bonding and/or fracture.

According to a third aspect, the invention relates to a method for measuring the propagation of a spacing zone C between a first portion and a second portion of at least one substrate, the method comprising the following steps:

emitting at least two incident beams, spatially distinct each illuminating a region of the substrate so that each generates at least a first emergent beam originating from the interface between the first portion and the spacing zone C, and at least one second emergent beam originating from the interface between the spacing zone C and the second portion, detecting the values of the resulting luminous intensity at a given point of the interference between the first and second emergent beams at a first detecting position, detecting the values of the resulting luminous intensity at a given point of the interference between the first and second emergent beams at a second detecting position, measuring the time difference between a first detecting instant of the occurrence of the spacing zone C at the first detecting position and a second detecting instant of the occurrence of the spacing zone C at the second detecting position, and determining the speed of propagation of the spacing zone C between the first and second portions of said at least one substrate depending on the time difference between the first and second detecting instants and on the distance between the first and second detecting positions.

This method allows thus observing easily in situ the very rapid propagation of a spacing zone C between two portions of a substrate during a fracture or a bonding. The use of light signals of an emergent beam of the substrate allows great sharpness and precision of measurements.

Advantageously, the surfaces of the first and second portions are polished on both sides so as to limit the diffusion of the beams.

Preferably, the method comprises a step consisting of selecting at least one incident beam such that at least 10% of its luminous intensity can be transmitted through the first traversed portion.

According to one possibility, the method further comprises a step consisting of detecting the occurrence of the spacing zone C in the substrate by a time variation of luminous intensity. The detection of the occurrence of the spacing zone C is performed on the scale of a few fractions of the optical wavelength, it allows measuring very low opening thicknesses.

This method also allows, if the place and instant of the initiation of bonding or fracture are known, determining the speed of propagation of the spacing zone C depending on the distance between the place of initiation of bonding or fracture and the detection point and the time between the moment of initiation of the fracture or the bonding and that of detection.

Advantageously, the method further comprises a step consisting of determining the elapsed time between at least two consecutive maxima of the luminous intensity detected by a detecting module so as to determine the speed of propagation of the spacing zone C between the first and second portions. This determination is very accurate because it uses an interferometric measurement. The spacing or approximation profile between the two portions is obtained at a position determined by the position of the considered photodetector. The profile can be obtained for each of the positions of the used photodetectors. It is therefore possible, if different systems are used, to determine the dynamic profile of bonding or fracture.

According to a particular embodiment of the invention, the method comprises the following steps:

implementing several substrates transmitting at least 10% of the luminous intensity of the emitted beams Fi, and emitting at least one incident beam such that it passes through each first portion, each second portion and each spacing zone C.

In this way, it is possible to detect the occurrence of a spacing zone C, the speed of propagation of the spacing zone C and the spacing profile between the first and second portion of several substrates in a single step of data acquisition.

Other aspects, aims and advantages of the present invention will be better apparent upon reading the following description of various embodiments thereof, given by way of non-limiting examples and made with reference to the accompanying drawings. The figures do not necessarily respect the scale of all the elements shown so as to improve their readability. Dotted lines symbolize first and second portions of a substrate delimited by an embrittlement plane. Following the description, for the sake of simplification, identical, similar or equivalent elements of different embodiments have the same numerical references.

Figure 1:
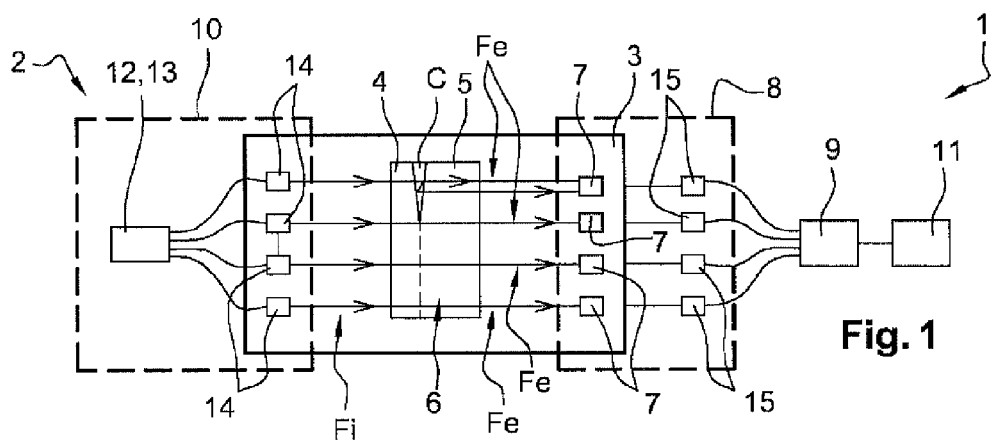
FIG. 1 is a schematic illustration of a measuring system according to an embodiment of the invention.

FIG. 1 illustrates a device 1 suitable for the propagation of a spacing zone C comprising a measuring system 2 for measuring the propagation of the spacing zone C and a measuring bench 3, equipped with means particularly suitable for the induction of a fracture between a first portion 4 and a second portion 5 of a substrate 6, for example in silicon. The bench 3 may be for example an enclosure of fracture, such as a furnace.

The measuring system 2 comprises an emitting module 10 for emitting four incident beams Fi suitable for passing through a second portion 5 and/or a first portion 4 forming a substrate 6 placed in the enclosure 3. The measuring system 2 also comprises a detecting module 8 including receivers 7 for receiving and detecting emergent beams Fe. The detecting module 8 also comprises photodiodes 15 which convert the optical signals received by the receivers 7 into electric current. The measuring system 2 finally comprises acquisition and recording devices of the signals 9 and a calculator 11 suitable for the determination of the parameters of the dynamics of propagation of the spacing zone C between the first portion 4 and the second portion 5 of the substrate 6.

Note that the measuring system 2 as illustrated in FIG. 1 is presented for an operation in a transmitting mode that is to say that the emitting module 10 and the detecting module 8 are placed facing each other, on either sides of the substrate 6. This operation in transmission is only suitable when the two portions 4, 5 of the substrate 6 are sufficiently transparent to the beams, that is to say they transmit at least 10% of the luminous intensity of the beams Fi.

The emitting module 10 is constituted of a light source 12 able to emit a beam that is monochromatic, coherent and intense, such as an infrared laser diode. A generator, not shown, allows driving the transparent infrared laser diode 12 for the silicon.

Then, the emitting module 10 comprises successively, in the direction of the optical path traveled by the beams, a coupler 13 which divides the light emitted by the laser diode 12 into four monochromatic beams. Four single-mode optical fibers convey these beams respectively to four collimators 14, placed in the enclosure 3 allowing the fracture. The incident beams Fi produced by the collimators 14 are parallel and coplanar. Incident beams Fi may also not be coplanar. They can be emitted toward different points distributed over the entire main surface of the substrate 6.

A nacelle suitable for fracture (not illustrated) is disposed in the enclosure 3 to insert therein the substrate 6 such that the four incident beams Fi can pass through both portions 4, 5 of the transparent substrate 6 as well as the embrittlement plane.

A detecting module 8 comprising four receivers 7 and four photodetectors 15 is placed symmetrically to the collimators 14 so as to receive the emergent beams Fe of the substrate 6. In the example, four optical fibers, for example single-mode or multi-mode optical fibers, are provided for transmitting the optical signals to the outside of the enclosure 3, up to four photodetectors 15, such as photodiodes.

The photodetector 15 is suitable for the conversion of the values of luminous intensity of the four emergent beams Fe received by the four receivers 7 into electrical signals in order to transmit them to acquisition and recording devices 9, such as a digital oscilloscope, by way of electric cables. A connecting cable allows the transmission of information recorded for processing with a calculator 11, such as a processor. In an alternative embodiment, not shown, the acquisition and recording devices 9 are integrated in the calculator 11.

In a non illustrated embodiment, all of the the elements composing the emitting module 10 and the detecting module 8 are all placed in the enclosure 3.

A first example of operation of the measuring system 2 is now described for measuring the fracture of a substrate 6 composed of two portions 4, 5 of silicon. These two portions 4, 5 are delimited by an embrittlement plane previously obtained by the implantation of ionic species in the substrate 6 and at which level the fracture can be induced for example by heat treatment, possibly assisted by a mechanical action such as the insertion of a blade. Other origins of embrittlement may be used for obtaining a cleavage in such a substrate 6.

The emission wavelength of the laser diode 12 is selected to be greater than 1100 nm, and for example equal to 1310 nm so as to pass through the portions 4, 5 of silicon. In fact, silicon is a transparent material at these wavelengths. It can transmit more than 10% of the luminous intensity of the beam of such a wavelength. In the example, the power of the laser diode 12 is of 5 mW, this allows generating four 1.25 mW beams.

When the substrate 6 is placed in the nacelle of the enclosure 3, the incident beams Fi pass through the substrate 6. The received emergent beams Fe present a constant luminous intensity as a function of time.

Then a heat treatment is applied in the enclosure 3 so as to cause the fracture of the substrate 6 at the embrittlement plane. A mechanical stress for example made by a blade (not shown) at the embrittlement plane can complete the effect of the thermal budget applied to the substrate 6 and finalize the initiation of the fracture. At the instant when the fracture is initiated, a spacing zone C (or air corner) appears between two portions 4, 5 which are spaced apart, as illustrated by magnification in FIG. 1. Once initiated, the fracture front then moves very quickly along the embrittlement plane.

The ray path is illustrated in a simplified manner in FIG. 1. An emitted beam Fi is divided at the air corner. A first part of the incident beam is directly transmitted through the first portion 4, the air corner C and the second portion 5, thereby forming a first emergent beam Fe. Due to the presence of spacing zone C, a second emitted beam part Fi is reflected at the interface between the air corner C and the second portion 5, this beam is again partially reflected at the interface between the first portion 4 and the air corner C, which forms a second emergent beam Fe very close to the first emergent beam Fe. These first and second beams Fe interfere with each other and the values of luminous intensity resulting from the interference are received by the receivers 7. The difference in optical path between the first and second beams Fe corresponds as a first approximation to twice the distance between the two portions 4, 5, namely twice the thickness of the spacing zone C. Therefore, when the fracture front or the spacing zone C passes through a first incident beam Fi, it causes the formation of an interference received by the detecting module 8. This variation results in a variation of the received luminous intensity at the corresponding photodetector 15 which becomes sinusoidal and characteristic of an interference signal. This variation allows identifying the instant of occurrence of the spacing zone C and thus the fracture at the concerned photodetector 15. The variation of the luminous intensity is converted into an electrical signal which is recorded at the oscilloscope 9 and transmitted to the processor 11.

With the progression of the fracture front between the two portions 4, 5, the air corner C passes successively through a second incident beam Fi and a third and a fourth incident beam Fi so that a change in luminous intensity is detected successively by second, third and fourth corresponding photodetectors 15. These variations of luminous intensity are converted into variations of electric current intensity which can be observed for example on the screen of the oscilloscope 9 for a better understanding of the phenomenon.

Figure 2:
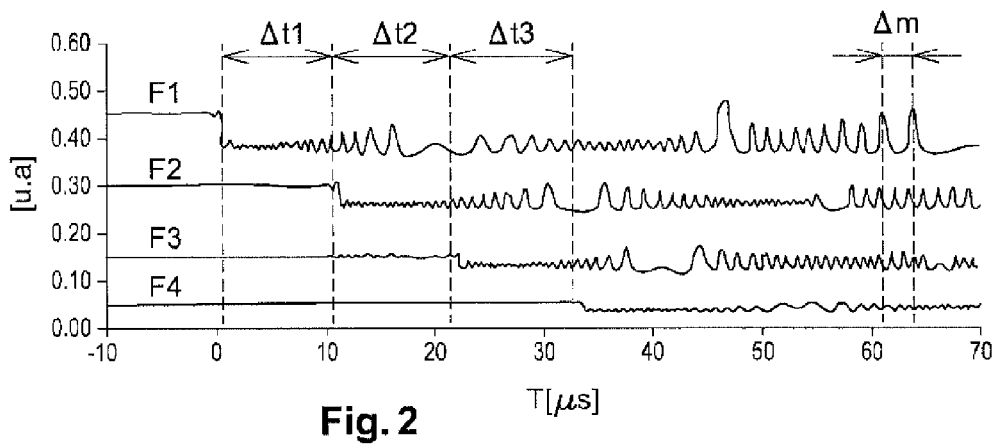
FIG. 2 is a schematic illustration of electrical signals obtained by different photodetectors according to an embodiment of the invention.

FIG. 2 shows an oscilloscope screen showing the electrical signals that have been transmitted thereto by each of the photodetectors 15, as a function of time. The electrical signal F1 represented in the uppermost part of the screen corresponds to the variation of the electric current intensity and thus the variation of the luminous intensity detected by a first photodetector 15. Between the values of time T of −10 and 0 microseconds, the electric current intensity is constant because there is no spacing zone C (or air corner) at the implanted brittle zone. When T is at 0 microseconds, the intensity of current drops vertically which means that the air corner C has passed through the first beam. This variation of intensity allows detecting the occurrence of the air corner C by the first photodetector 15 at the first detecting position.

The electrical signal F2 represented below corresponds to the variation of luminous intensity of the second emergent beam Fe. Before a time of 10 microseconds, the intensity is constant then at 10 microseconds the intensity drops vertically. This signifies that the air corner C has passed through the second incident beam Fi and has been detected by the second photodetector 15 at a second detecting position. Similarly, the occurrence of the air corner C was then detected by the third photodetector 15 to 21 microseconds (electrical signal F3) at a third detecting position and then by the fourth photodetector 15 to 33 microseconds (electrical signal F4) at a fourth detecting position. The measuring system 2 therefore allows detecting the instants of occurrence of the fracture front, in situ, at different detecting positions.

From these informations, the processor 11 can measure the time difference Δt between a first detecting instant of occurrence of the air corner C at a first position and a second detecting instant of occurrence of the air corner C at a second detecting position. Knowing the distance between the two detecting positions, namely the distance of the points on the substrate 6 at which the signals penetrate the substrate 6 or the distance between the two corresponding incident Fi or emergent Fe beams at the substrate 6, the processor 11 may calculate the speed of propagation of the air corner C and the speed of the fracture front in the entire substrate 6 or at different points of the substrate 6. In the example above, the speed of propagation of the fracture front is in the range of 1.5 km/s.

Furthermore, the processor 11 may also determine the time elapsed between two consecutive maxima Δm of each electrical signal. Knowing that between the two maxima Δm, the obtained spacing between the two portions 4, 5 has evolved by half the wavelength of the incident beam Fi, the processor 11 can calculate the spacing speed of the portions 4, 5, and that is for each detecting position.

Similarly, it is possible to determine the dynamics of the spacing profile. In fact, if we consider the spacing zone C as a dihedral the apex of which corresponds to the point of contact between the surfaces of the first portion 4 and the second portion 5, the greater the intensity of oscillations, the more the dihedral opens up (the more the angle at the base is significant). Therefore it is observed that when the air corner appears, the dihedral opens up progressively then we note a "cusp" corresponding to oscillations with increasingly low amplitudes: the two portions 4, 5 after being spaced apart, tighten due to the external pressure. Then the amplitude of the oscillations increase again.

Therefore the measuring system 2 allows determining several parameters representative of the conditions of propagation of a spacing zone C. This measuring system 2 indeed allows detecting the instant when the fracture is initiated in situ in the enclosure 3 of fracture, the speed of progression of the fracture front and the spacing profile of the portions 4, 5 of the substrate 6. From these informations, it is then possible to determine the intensity and variation of stresses submitted on the portions 4, 5 during the fracture and also to study and determine the rupture mechanism.

The portions 4, 5 of the observed substrates 6 can be for example made of semiconductor materials such as silicon, ceramics or glass. The materials of both portions 4, 5 can be identical or different according to the desired purpose. The first or second portions 4, 5 may also be made of two materials bonded together, in particular to obtain a stiffening effect when detaching a thin film during a Smart Cut™ process. The material serving as a stiffener can be transparent at the used wavelength such that the measuring system 2 may operate in a transmitting mode.

When the material is not transparent, this one is preferably used in the second portion 5 of the substrate 6 which receives the beams after the first portion 4. The measuring system 2 is therefore suitable for operating in a reflection mode, FIG. 3 shows the simplified and enlarged path of the beams.

In this second example of operation of the measuring system 2 in the reflection mode, the emitting module 10 of the beams is placed on the same side of the substrate 6 as the detecting module 8. The measuring system 2 observes the fracture of a substrate 6, the first portion 4 of which is transparent at the used wavelength but the second portion 5 of which reflects the incident beam Fi.

In this case, a portion of the incident beam Fi is reflected at the interface between the air corner C and the first portion 4 so as to form an emergent beam Fe. Another portion of the incident beam Fi is reflected at the interface between the air corner C and the second portion 5, which forms a second emergent beam Fe. The first and second emergent beams Fe thus generated interfere and create interference fringes detected by the detecting module 8. The difference in optical path between these first and second beams Fe corresponds as a first approximation to twice the distance between the two portions 4, 5, namely twice the thickness of the spacing zone C.

Figure 3:
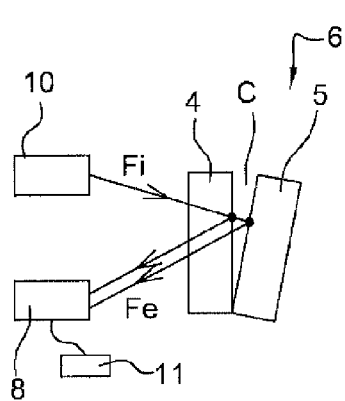
FIG. 3 is a schematic illustration of a part of a measuring system for operation in a reflection mode according to an embodiment of the invention.

The other elements of the measuring system 2 of FIG. 3 may be similar to those described above. In the same way as for the first example, the optical signal measured by the detecting module 8 is constant before the occurrence of the fracture. The signal begins to oscillate upon occurrence of the spacing zone C. After the passage of the fracture front, the calculator 11 can determine the instant of occurrence of the fracture. When a plurality of beams Fi are emitted (not shown), it is also possible to measure the speed of the fracture front and spacing profile of the portions 4, 5 so as to determine the fracture mechanism in the same way as in the described first example.

Figure 4:
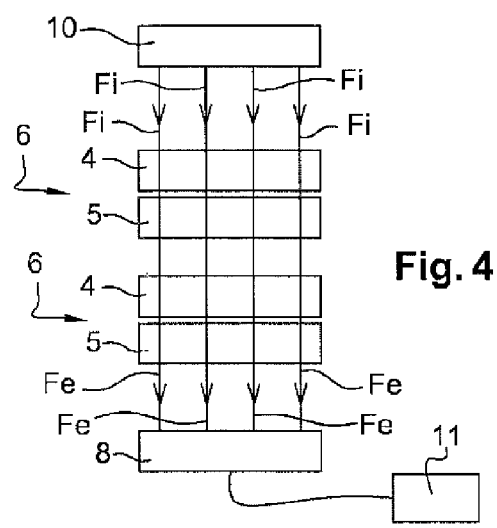
FIG. 4 is a schematic illustration of a measuring system for which the measurement is performed on a plurality of substrates according to an embodiment of the invention.

FIG. 4 illustrates a part of a measuring system 2 according to a third example without magnifying the path of the different beams. The device operates in a transmitting mode for measuring propagation of a spacing zone C in several substrates 6 in a single measuring step. Particularly shown are corresponding emitting module 10 of four incident beams Fi and detecting module 8 facing each other. The other parts of the measuring system 2 which are not shown in FIG. 4 can be identical to those shown in FIG. 1.

This third example shows the bonding between a plurality of first portions 4 and a plurality of second portions 5 so as to form a plurality of substrates 6. The two first portions 4 and two second portions 5 are put in contact respectively pairwise in a nacelle of the enclosure 3 equipped with means suitable for inducing bonding between the portions. The two portions 4, 5 are made of silicon such that an infrared laser diode 12 having an emission wavelength of 1310 nm can be used so that the measuring system 2 may operate in a transmitting mode.

In operation, each beam Fi emitted by the emitting module 10 therefore passes through the first and second transparent portions 4, 5 of the first substrate 6 then the first and second transparent portions 4, 5 of the second substrate 6. Each emergent beam Fe of all of the substrates 6 is then received by a photodetector 15 of the detecting module 8 which converts it into an electrical signal for a processing by the calculator 11. Similarly as in a fracture, the intensity of the optical signal varies depending on the presence or not of an air corner between each portion 4, 5 and its propagation. It is then possible to determine in situ, with appropriate calculations, the instant of occurrence of the bonding front, the speed of bonding propagation and the spacing profile (or approximation) of the substrate 6 portions during the progression by the bonding wave by interferometry. It is understood here that the spacing profile is measured on a spacing zone between the portions 4, 5 that decreases with the progression of the bonding front.

This measuring system 2 thus allows measuring parameters of the propagation conditions of a spacing zone C during bonding of two portions 4, 5 of a plurality of substrates 6, in a single measuring step. It is therefore possible to determine the dynamics of bonding.

It is also possible to proceed identically in order to determine parameters of fracture of a plurality of substrates 6 in a single measuring step.

Furthermore, the emitting module 10 of the measuring system 2 may emit a larger number of beams Fi so as to be able to adapt the measurement to the dimensions of the substrates 6 to be observed. Similarly, analysis models may be modified depending on the nature of the materials of the substrates 6.

Therefore, the present invention proposes a measuring system 2, a device 1 suitable for the propagation of a spacing zone C comprising the measuring system 2 and a measuring method which allow measuring in situ fracture or bonding phenomena, at very high speeds of propagation. The use of optical beams allows maintaining very high accuracy and sensitivity of measurements despite the speed of the observed phenomena. Furthermore, the nature of the light source 12 may be adapted according to the nature of the material to be observed and it is possible to obtain measurements on a plurality of substrates 6 in a single step of data acquisition.

It goes without saying that the invention is not limited to the embodiments described above as examples but that it comprises all the technical equivalents and alternatives of the described means as well as their combinations.

The invention claimed is:

1. A measuring system for measuring the propagation of a spacing zone between a first portion and a second portion of at least one substrate, the system comprising:
    an emitting module for emitting at least two spatially distinct incident beams, each illuminating a region of the substrate, said emitting module being arranged so that the at least two incident beams are able to pass through the first portion and the spacing zone, and meet the second portion in such a way that each generates at least one first emergent beam originating from the interface between the first portion and the spacing zone, and at least a second emergent beam originating from the interface between the spacing zone and the second portion,
    a detecting module for detecting luminous intensity, arranged in order to detect the values of the resulting luminous intensity at a given point of the interference between the first and second emergent beams, and
    a calculator arranged to determine at least one parameter representative of the conditions of propagation of the spacing zone from the time variations of the luminous intensity detected by the detecting module.

2. The measuring system according to claim 1, wherein the detecting module and the computer are configured to determine speeds of propagation of the spacing zone between the first and second portions.

3. The measuring system according to claim 1, wherein the at least two incident beams are arranged so as to be coplanar in order to allow measuring the propagation of the spacing zone in the direction of the plane of the beams.

4. The measuring system according to claim 1, wherein the emitting module comprises a light source and at least one coupler, the light source and said at least one coupler being arranged such that said at least one coupler can separate the light emitted by the light source into at least two beams.

5. The measuring system according to claim 4, wherein the emitting module comprises at least two single-mode optical fibers and at least collimators, the optical fibers being suitable for guiding the beams produced by said at least one coupler respectively up to the collimator, the collimators being suitable for producing the at least two incident beams.

6. The measuring system according to claim 4, wherein the light source is monochromatic and comprises in particular a laser, such as an infrared laser diode.

7. The measuring system according to claim 1, wherein the emitting module is arranged to generate at least two incident beams which are monochromatic, coherent and intense such that the detected luminous intensity is greater than the noise of the detecting measurement.

8. The measuring system according to claim 1, wherein at least one incident beam is selected so that at least 10% of its luminous intensity can be transmitted through the first portion.

9. The measuring system according to claim 8, wherein the emitting module and the detecting module are arranged at the same side of said at least one substrate.

10. The measuring system according to claim 8 wherein at least one incident beam is also selected so that at least 10% of its luminous intensity can be transmitted through the second portion encountered by said at least one incident beam and in that the emitting module and the detecting module are arranged on either sides of said at least one substrate.

11. The measuring system according to claim 1, wherein the detecting module comprises at least one receiver of luminous intensity and at least one photodetector so as to convert the received values of resulting luminous intensity at a given point of interference between the first and second emergent beams, into an electrical signal.

12. The measuring system according to claim 11, comprising acquisition and recording means of the electrical signal, such as a sampling device in particular a digital oscilloscope or an analog-digital converter card.

13. A device suitable for propagating a spacing zone between a first portion and a second portion of at least one substrate, comprising a measuring bench such as a furnace, a traction machine or a testing machine, equipped with means adapted to the induction of a fracture or a bonding between the first portion and the second portion and a measuring system for measuring the propagation of a spacing zone according to claim 1.

14. A measuring method for measuring the propagation of a spacing zone between a first portion and a second portion of at least one substrate, comprising the following steps:
    emitting at least two incident beams, spatially distinct so that each generates at least one first emergent beam originating from the interface between the first portion and the spacing zone, and at least one second emergent beam originating from the interface between the spacing zone and the second portion,
    detecting the values of the resulting luminous intensity at a given point of interference between the first and second emergent beams at a first detecting position,
    detecting the values of the resulting luminous intensity at a given point of interference between the first and second beams at a second detecting position,
    measuring the time difference between a first detecting instant of the occurrence of the spacing zone at the first detecting position and a second detecting instant of the occurrence of the spacing zone at the second detecting position, and
    determining the speed of propagation of the spacing zone between the first and second portions of said at least one substrate depending on the distance between the first and second detecting positions and the difference of time between the first and second detecting instants $\Delta t$.

15. The measuring method according to claim 14, comprising a step of determining the elapsed time between at least two consecutive maxima $\Delta m$ of the luminous intensity detected by a detecting module so as to determine the speed of propagation of the spacing zone between the first and second portions.

16. The measuring method according to claim 14, comprising the following steps:
    implementing a plurality of substrates transmitting at least 10% of the luminous intensity of the emitted beams, and
    emitting at least one incident beam so that it passes through each first portion, each second portion, and each spacing zone.

* * * * *